US012076520B2

(12) United States Patent
Levy

(10) Patent No.: US 12,076,520 B2
(45) Date of Patent: Sep. 3, 2024

(54) CONTROL OF EXOGENOUS AGENT CHARACTERISTICS IN MICROBUBBLE-MEDIATED ULTRASOUND PROCEDURES

(71) Applicant: INSIGHTEC, LTD., Tirat Carmel (IL)

(72) Inventor: Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 324 days.

(21) Appl. No.: 16/771,770

(22) PCT Filed: Dec. 11, 2018

(86) PCT No.: PCT/IB2018/001548
§ 371 (c)(1),
(2) Date: Jun. 11, 2020

(87) PCT Pub. No.: WO2019/116097
PCT Pub. Date: Jun. 20, 2019

(65) Prior Publication Data
US 2020/0391019 A1    Dec. 17, 2020

Related U.S. Application Data

(60) Provisional application No. 62/597,071, filed on Dec. 11, 2017, provisional application No. 62/597,073, (Continued)

(51) Int. Cl.
*A61M 37/00*     (2006.01)
*A61N 7/00*      (2006.01)
*A61N 7/02*      (2006.01)

(52) U.S. Cl.
CPC ........... *A61M 37/0092* (2013.01); *A61N 7/00* (2013.01); *A61N 7/02* (2013.01); *A61M 2205/50* (2013.01);
(Continued)

(58) Field of Classification Search
CPC .................. A61M 37/0092; A61N 2007/0039
See application file for complete search history.

(56) References Cited

U.S. PATENT DOCUMENTS 6,740,039 B1    5/2004   Rafter et al.
8,932,237 B2    1/2015   Shuki et al.
(Continued)

FOREIGN PATENT DOCUMENTS

CN    102946945 A    2/2013
CN    103842020 A    6/2014
(Continued)

OTHER PUBLICATIONS

Lai P, Tarapacki C, Tran WT, El Kaffas A, Lee J, Hupple C, Iradji S, Giles A, Al-Mahrouki A, Czarnota GJ, Breast tumor response to ultrasound mediated excitation of microbubbles and radiation therapy in vivo, Oncoscience, Mar. 24, 2016;3(3-4):98-108. (Year: 2016).*
(Continued)

*Primary Examiner* — Brandy S Lee
*Assistant Examiner* — Phoebe Anne Staton
(74) *Attorney, Agent, or Firm* — Morgan, Lewis & Bockius LLP

(57) ABSTRACT

Various approaches for microbubble-enhanced ultrasound treatment of target tissue include retrieving a treatment plan stored in memory; causing administration of an exogenous agent in accordance with the treatment plan; causing, in accordance with the treatment plan, an ultrasound transducer to transmit ultrasound waves to the target tissue and generate a focus therein in the presence of administered exogenous agent; receiving, from a monitoring system, a measured parameter value indicating a treatment condition in response to administration of the exogenous agent and transmission of
(Continued)

the ultrasound waves during treatment; and adjusting the treatment plan based at least in part on the measured parameter value.

25 Claims, 12 Drawing Sheets

Related U.S. Application Data filed on Dec. 11, 2017, provisional application No. 62/597,076, filed on Dec. 11, 2017.

(52) U.S. Cl.
CPC ... *A61M 2230/04* (2013.01); *A61M 2230/205* (2013.01); *A61N 2007/0004* (2013.01); *A61N 2007/0039* (2013.01); *A61N 2007/0052* (2013.01); *A61N 2007/0056* (2013.01); *A61N 2007/0073* (2013.01); *A61N 2007/0078* (2013.01); *A61N 2007/0095* (2013.01)

(56) References Cited

U.S. PATENT DOCUMENTS

| | | | |
|---|---|---|---|
| 2003/0204141 | A1 | 10/2003 | Levin et al. |
| 2008/0269668 | A1 | 10/2008 | Keenan et al. |
| 2008/0312535 | A1 | 12/2008 | Kawabata |
| 2009/0234231 | A1* | 9/2009 | Knight .................. A61M 5/172 600/458 |
| 2010/0106078 | A1 | 4/2010 | Dimitrova et al. |
| 2011/0270136 | A1 | 11/2011 | Vitek et al. |
| 2011/0293530 | A1 | 12/2011 | Hecht et al. |
| 2012/0175305 | A1 | 7/2012 | Borden et al. |
| 2012/0316439 | A1* | 12/2012 | Behar .................... A61B 5/015 600/439 |
| 2014/0236051 | A1* | 8/2014 | Kim ........................ A61N 7/02 601/3 |
| 2016/0008633 | A1 | 1/2016 | Vortman et al. |
| 2018/0206816 | A1 | 7/2018 | Prus et al. |
| 2019/0009109 | A1 | 1/2019 | Vortman et al. |
| 2019/0151146 | A1 | 5/2019 | Kim |
| 2019/0151239 | A1 | 5/2019 | Abrams et al. |

FOREIGN PATENT DOCUMENTS

| | | |
|---|---|---|
| JP | 2011-513030 A | 4/2011 |
| JP | 2016-508808 A | 3/2016 |
| WO | 2009/114278 A1 | 9/2009 |
| WO | WO2011/025893 A1 | 3/2011 |
| WO | WO2011/034892 A2 | 3/2011 |
| WO | 2013046076 A1 | 4/2013 |
| WO | WO2013/046076 A1 | 4/2013 |

OTHER PUBLICATIONS

Lentacker I, Geers B, Demeester J, De Smedt SC, Sanders NN, Design and evaluation of doxorubicin-containing microbubbles for ultrasound-triggered doxorubicin delivery: cytotoxicity and mechanisms involved, Mol Ther. Jan. 2010;18(1):101-8, Epub Jul. 21, 2009. (Year: 2009).*

International Search Report and Written Opinion dated Mar. 18, 2019 for International Application No. PCT/IB2018/001548 14 pages.

International Search Report and Written Opinion dated Apr. 9, 2019 for International Application No. PCT/IB2018/001603, 13 pgs.

International Preliminary Report on Patentability dated Jun. 16, 2020 for International Application No. PCT/IB2018/001603, 7 pgs.

International Search Report and Written Opinion dated Mar. 18, 2019 for International Application No. PCT/IB2018/001548, 11 pgs.

International Preliminary Report on Patentability dated Jun. 16, 2020 for International Application No. PCT/IB2018/001548, 7 pgs.

International Search Report and Written Opinion dated Jun. 4, 2019 for International Application No. PCT/IB2018/001537, 18 pgs.

First Office Action, CN201880089076.2, Sep. 24, 2021, 12 pgs.

First Office Action, CN201880088970.8, Sep. 16, 2021, 15 pgs.

First Office Action, CN201880087835.1, Nov. 11, 2021, 22 pgs.

Second Office Action, CN201880089076.2, Mar. 30, 2022.

Notice of Reasons for Refusal, JP2020531576, Jul. 29, 2022, 6 pgs.

Insightec Ltd., Communication Pursuant to Article 94(3), EP18852736.0, Mar. 30, 2022, 4 pgs.

Insightec Ltd., Communication Pursuant to Article 94(3), EP18845443.3, Mar. 29, 2022, 4 pgs.

Insightec Ltd., Communication Intention to Grant EP Patent, EP18842722.3, Feb. 11, 2022, 8 pgs.

Priscilla Lai et al., Breast tumor response to ultrasound mediated excitation of microbubbles and radiation therapy in vivo, Oncoscience, Advance Publications 2016, Mar. 24, 2016 (Year: 2016), 11 pgs.

Ine Lentacker, Design and Evaluation of Doxorubicin-containing Microbubles for Ultrasound-triggered Doxorubicin Delivery: Cytotoxicity and Mechanisms Involved, Molecular Therapy, Jan. 2010: vol. 18 No. 1, 101-108, Epub Jul. 21, 2009 (Year: 2009), 8 pgs.

Levy, Office Action, U.S. Appl. No. 16/771,770, Aug. 10, 2022, 16 pgs.

Vortman, Office Action, U.S. Appl. No. 16/771,768, Sep. 9, 2022, 14 pgs.

Vortman, Final Office Action, U.S. Appl. No. 16/771,768, Nov. 8, 2022, 12 pgs.

Zadicario, Office Action, U.S. Appl. No. 16/771,771, Dec. 23, 2022, 20 pgs.

International Search Report in corresponding Japanese Application No. 2020-531629, dated Nov. 20, 2023, 6 pages, with English translation.

* cited by examiner

CONTROL OF EXOGENOUS AGENT CHARACTERISTICS IN MICROBUBBLE-MEDIATED ULTRASOUND PROCEDURES

CROSS-REFERENCE TO RELATED APPLICATION

This application is a U.S. National Phase Application of PCT/IB2018/001548, filed Dec. 11, 2018, which claims the benefit of and priority to U.S. Provisional Patent Applications Nos. 62/597,071, 62/597,076 and 62/597,073 (all filed on Dec. 11, 2017). The entire disclosures of these priority documents are hereby incorporated by reference.

FIELD OF THE INVENTION

The present invention relates, generally, to microbubble-mediated ultrasound procedures, and more particularly to systems and methods for controlling characteristics of an exogenous agent carrying microbubbles.

BACKGROUND

Focused ultrasound (i.e., acoustic waves having a frequency greater than about 20 kiloHertz) can be used to image or therapeutically treat internal body tissues within a patient. For example, ultrasound imaging systems produce images of body tissue by transmitting ultrasound waves to the body tissue and detecting and analyzing echoes reflected therefrom. In addition, ultrasound waves may be used in applications involving ablation of tumors, targeted drug delivery, disruption of the blood-brain barrier (BBB), lysing of clots, and other surgical procedures. During imaging and/or tumor ablation, a piezoceramic transducer is placed externally to the patient, but in close proximity to the tissue to be imaged and/or ablated (i.e., the target region). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

During a focused ultrasound procedure, small gas bubbles (or "microbubbles") may be generated within and/or introduced into the target region. Depending on the amplitude and frequency of the applied acoustic field, the microbubbles may oscillate or collapse (this mechanism is called "cavitation") and thereby cause various thermal effects in the target region and/or its surrounding region. For example, cavitation of microbubbles may enhance energy absorption at the ultrasound focal region such that the tissue therein is heated faster and ablated more efficiently than would occur in the absence of microbubbles. This effect and the response of the microbubbles to the ultrasound waves together are referred to herein as the "microbubble response." In treatments involving the central nervous system, microbubble cavitation may cause disruption of blood vessels, thereby inducing "opening" of the BBB for enhancing targeted drug delivery. Further, microbubbles may be employed for contrast-enhanced ultrasound imaging, drug and gene delivery and/or metabolic gas delivery.

Typically, microbubbles are intravenously introduced into the patient's bloodstream. To avoid potential hazards from gas in the circulatory system, the number of injections and volume of injected microbubbles in a treatment is limited. This limitation presents challenges to the microbubble-enhanced ultrasound procedure, however, particularly when the target tumor tissue spans a large area and/or multiple target tumors are identified for treatment. In addition, an uncontrolled microbubble cavitation event may result in undesired damage to and around the target region. For example, ablating cells forming portions of the BBB may not only compromise BBB function but also cause unwanted cell death or necrosis in surrounding, non-target tissue. To minimize the undesired effects of microbubble cavitation during disruption of the target region, one conventional approach utilizes a passive cavitation detector that measures the acoustic response of the microbubbles after each ultrasound sonication. The tissue disruption, however, may result from other microbubble characteristics (e.g., size, concentration, or the administration profile). For example, the magnitude and number of BBB openings may correlate with microbubble sizes and/or concentrations. Further, acoustic properties (e.g., the spatial power distribution, the temporal power distribution or the shape of the focal zone) of the ultrasound pulses applied to the microbubbles may affect the tissue disruption.

Accordingly, there is a need for advance treatment planning as well as real-time monitoring techniques that permit the effects of the microbubbles on tissue to be accurately gauged, thereby enabling adjustment of microbubble administration so as to optimize the performance of the procedure (e.g., effects on the target region) while avoiding damage to non-target regions.

SUMMARY

The present invention relates to microbubble-enhanced ultrasound procedures that employ an ultrasound system, a monitoring system and a microbubble administration system. In various embodiments, prior to the ultrasound procedure, the monitoring system detects information about the patient (e.g., the patient's physiological condition and/or anatomic characteristics of the target and/or non-target regions). For example, the monitoring system may include one or more biosensors for measuring a physiological parameter (e.g., the blood pressure, blood circulation rate, blood perfusion rate, and/or heart rate) of the patient. Alternatively or additionally, the monitoring system may include an imager for monitoring tissue characteristics (e.g., the size, location, structure, shape or temperature) of the target and/or non-target regions. In one embodiment, the monitoring system includes an acoustic-signal detector for measuring acoustic signals from the target and/or non-target regions. Based on the parameter(s) detected by the monitoring system, a computational facility may generate a treatment plan for the target region. The treatment plan may include, for example, a disruption rate profile of the target tissue, characteristics (e.g., a type, a dose, a concentration profile, a temperature, or an administration profile) of an exogenous agent (e.g., an ultrasound contrast agent) carrying the microbubbles and/or one or more therapeutic agents for treating the target, and/or an acoustic power profile of the ultrasound system. Generally, the microbubbles are homogeneously formed and suspended in the exogenous agent; therefore, controlling the characteristics (e.g., volume or concentration) of the exogenous agent may directly affect the characteristics of the microbubbles. Hence, as used herein, the term "exogenous agent" refers to a composition including a liquid carrier with microbubbles, nanobubbles, mixtures of several types of bubbles and/or drugs encapsulated in bubbles dispersed therein. Typically, an exogenous agent will contain microbubbles exhibiting a desired characteristic, e.g., conforming to a maximal size, a size distribution or a size limit.

During treatment, the ultrasound system and administration system of the therapeutic agent(s) and/or exogenous agent are activated and operated in accordance with the treatment plan. In addition, the monitoring system may in real-time detect signals from the target and/or non-target regions and provide the detected signals to the computational facility. The computational facility can then update the treatment plan based on the real-time feedback and cause the ultrasound system and/or the administration system of the therapeutic agent(s) and exogenous agent to operate in accordance with the updated treatment plan, thereby optimizing treatment effects on the target region and avoiding damage to the non-target region.

Generally, the ultrasound procedure may involve treating the target region (e.g., opening the BBB and/or ablating a target tumor) or imaging the target region and/or non-target region (e.g., regions surrounding the target region and/or intervening regions located between the target region and the ultrasound system). Although the description herein only refers to an ultrasound treatment procedure for ease of reference, it should be understood that the same approaches apply as well to an ultrasound imaging procedure.

Accordingly, in one aspect, the invention pertains to a system for microbubble-enhanced treatment of target tissue. In various embodiments, the system includes an ultrasound transducer having multiple transducer elements; an administration device for administering an exogenous agent; a monitoring system for measuring one or more parameter values associated with the ultrasound transducer, the exogenous agent, the target tissue and/or non-target tissue; computer memory storing a treatment plan; and one or more controllers. The controller(s) may be configured to (a) cause administration of the exogenous agent; (b) cause the ultrasound transducer to transmit ultrasound waves to the target tissue and generate a focus therein in the presence of administered exogenous agent; (c) receive, from the monitoring system, the measured parameter value(s) indicating a treatment condition in response to administration of the exogenous agent and transmission of the ultrasound waves during treatment; and (d) adjust the treatment plan based at least in part on the measured parameter value(s). In one embodiment, the ultrasound transducer, monitoring system, and administration device are controlled by three separate, intercommunicating controllers. In another embodiment, the ultrasound transducer and monitoring system are controlled by the first controller and the administration device is controlled by the second controller; the first and second controllers are in communication with each other. In addition, the measured parameter value(s) may be indicative of the treatment condition of the target tissue and/or non-target tissue in response to an interaction between the administered exogenous agent and the transmitted ultrasound waves.

The monitoring system may include, for example, a biosensor; the measured parameter value(s) may include one or more physiological parameter values, such as a blood pressure, a blood circulation rate, a blood perfusion rate, a blood oxygen level and/or a heart rate. In one embodiment, the treatment plan specifies a characteristic such as a type, a dose, a concentration profile, a temperature and/or an administration profile (e.g., an administration rate, an administration timing and/or an administration pressure) of the exogenous agent; the controller is further configured to adjust the characteristic of the exogenous agent based at least in part on the measured physiological parameter value(s). Additionally or alternatively, the treatment plan may specify a disruption rate profile of the target tissue; the controller may be further configured to adjust the characteristic of the exogenous agent based at least in part on the disruption rate profile. In some embodiments, the treatment plan specifies an acoustic power profile associated with the ultrasound transducer (e.g., amplitudes, frequencies, phases, directions and/or activation time associated with the transducer, and/or time intervals between consecutive series of sonications); the controller is further configured to adjust the acoustic power profile based at least in part on the adjusted characteristic of the exogenous agent. In various embodiments, the administration device is further configured to administer the exogenous agent carrying microbubbles, and the treatment plan specifies a characteristic (e.g., a diameter, a size distribution, a shell composition, a gas composition and/or a liquid core composition) of the microbubbles.

Additionally or alternatively, the monitoring system may include an imager; the measured parameter value(s) may include a tissue characteristic (e.g., a temperature, a structure, a size, a shape and/or a location) of the target tissue and/or the non-target tissue. In one embodiment, the treatment plan specifies a characteristic such as a type, a dose, a concentration profile, a temperature and/or an administration profile (e.g., an administration rate, an administration timing and/or an administration pressure) of the exogenous agent; the controller is further configured to adjust the characteristic of the exogenous agent based at least in part on the measured tissue characteristic of the target tissue and/or non-target tissue.

In various embodiments, the monitoring system includes an acoustic-signal detector; the measured parameter value(s) includes ultrasound reflections and/or emissions from the target tissue and/or non-target tissue. The treatment plan may specify a characteristic such as a type, a dose, a concentration profile, a temperature and/or an administration profile (e.g., an administration rate, an administration timing and/or an administration pressure) of the exogenous agent; the controller may be configured to adjust the characteristic of the exogenous agent based at least in part on the measured ultrasound reflections and/or emissions. In one embodiment, the treatment plan specifies an acoustic power profile associated with the ultrasound transducer (e.g., amplitudes, frequencies, phases, directions and/or activation time associated with the transducer, and/or time intervals between consecutive series of sonications); the controller is further configured to adjust the acoustic power profile based at least in part on the adjusted characteristic of the exogenous agent and/or the measured ultrasound reflections and/or emissions. In addition, the system may further include a radiation device for transmitting a radiation dose to the target tissue.

In various embodiments, the system further includes the second administration device for administering a therapeutic agent to the target tissue. The therapeutic agent may include Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, and/or Cytarabine (cytosine arabinoside, ara-C)/ara-U. In addition, the treatment plan specifies a characteristic (a type, a dose, a concentration profile, a temperature, an administration rate, an administration timing and/or an administration pressure) of the therapeutic agent, and the controller is configured to adjust the characteristic of the therapeutic agent based at least in part on the measured physiological parameter value(s).

In another aspect, the invention relates to a method of treating target tissue. In various embodiments, the method includes (a) retrieving a treatment plan electronically stored in computer memory; (b) causing administration of an exogenous agent in accordance with the treatment plan; (c) causing, in accordance with the treatment plan, an ultrasound transducer to transmit ultrasound waves to the target tissue and generate a focus therein in the presence of administered exogenous agent; (d) receiving, from a monitoring system, one or more measured parameter values indicating a treatment condition in response to administration of the exogenous agent and transmission of the ultrasound waves during treatment; and (e) adjusting the treatment plan based at least in part on the measured parameter value(s). The measured parameter value(s) may be indicative of the treatment condition of the target tissue and/or non-target tissue in response to an interaction between the administered exogenous agent and the transmitted ultrasound waves.

The measured parameter value(s) may be, for example, a physiological parameter value, such as a blood pressure, a blood circulation rate, a blood perfusion rate, a blood oxygen level and/or a heart rate. In one embodiment, the treatment plan specifies a characteristic of the exogenous agent; the method further includes adjusting the characteristic such as a type, a dose, a concentration profile, a temperature and/or an administration profile (e.g., an administration rate, an administration timing and/or an administration pressure) of the exogenous agent based at least in part on the measured physiological parameter value(s). Additionally or alternatively, the treatment plan may specify a disruption rate profile of the target tissue; the method further includes adjusting the characteristic of the exogenous agent based at least in part on the disruption rate profile. In some embodiments, the treatment plan specifies an acoustic power profile associated with the ultrasound transducer (e.g., amplitudes, frequencies, phases, directions and/or activation time associated with the transducer, and/or time intervals between consecutive series of sonications); the method further includes adjusting the acoustic power profile based at least in part on the adjusted characteristic of the exogenous agent. In various embodiments, administration of the exogenous agent causes administration of microbubbles; the treatment plan specifies a characteristic (e.g., a diameter, a size distribution, a shell composition, a gas composition and/or a liquid core composition) of the microbubbles.

Additionally or alternatively, the measured parameter value(s) may include a tissue characteristic (e.g., a temperature, a structure, a size, a shape and/or a location) of the target tissue and/or the non-target tissue. In one embodiment, the treatment plan specifies a characteristic such as a type, a dose, a concentration profile, a temperature and/or an administration profile (e.g., an administration rate, an administration timing and/or an administration pressure) of the exogenous agent; the method further includes adjusting the characteristic of the exogenous agent based at least in part on the measured tissue characteristic of the target tissue and/or the non-target tissue.

Additionally or alternatively, the measured parameter value(s) may includes ultrasound reflections and/or emissions from the target tissue and/or non-target tissue. The treatment plan may specify a characteristic such as a type, a dose, a concentration profile, a temperature and/or an administration profile (e.g., an administration rate, an administration timing and/or an administration pressure) of the exogenous agent. The method may further include adjusting the characteristic of the exogenous agent based at least in part on the measured ultrasound reflections and/or emissions. In one embodiment, the treatment plan specifies an acoustic power profile associated with the ultrasound transducer (e.g., amplitudes, frequencies, phases, directions and/or activation time associated with the transducer, and/or time intervals between consecutive series of sonications); the method further includes adjusting the acoustic power profile based at least in part on the adjusted characteristic of the exogenous agent and/or the measured ultrasound reflections and/or emissions. In addition, the method may further include transmitting a radiation dose to the target tissue.

In various embodiments, the method further includes causing administration of a therapeutic agent to the target tissue. The therapeutic agent may include Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, and/or Cytarabine (cytosine arabinoside, ara-C)/ara-U. In addition, the treatment plan specifies a characteristic (a type, a dose, a concentration profile, a temperature, an administration rate, an administration timing and/or an administration pressure) of the therapeutic agent; the method further includes adjusting the characteristic of the therapeutic agent based at least in part on the measured physiological parameter value(s).

Another aspect of the invention relates to a system for microbubble-enhanced treatment of target tissue. In various embodiments, the system includes an ultrasound transducer; an administration device for an exogenous agent and/or a therapeutic agent; computer memory storing a treatment plan that specifies a series of operations of the ultrasound transducer and the administration device so as to achieve a desired treatment effect on the target tissue; and a controller configured to drive the ultrasound transducer and administration device based at least in part on the treatment plan. In one implementation, the system further includes a monitoring system for measuring one or more parameter values associated with the ultrasound transducer, the exogenous agent, the therapeutic agent, the target tissue, and/or non-target tissue. The controller is further configured to adjust the treatment plan based at least in part on the measured parameter value(s).

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
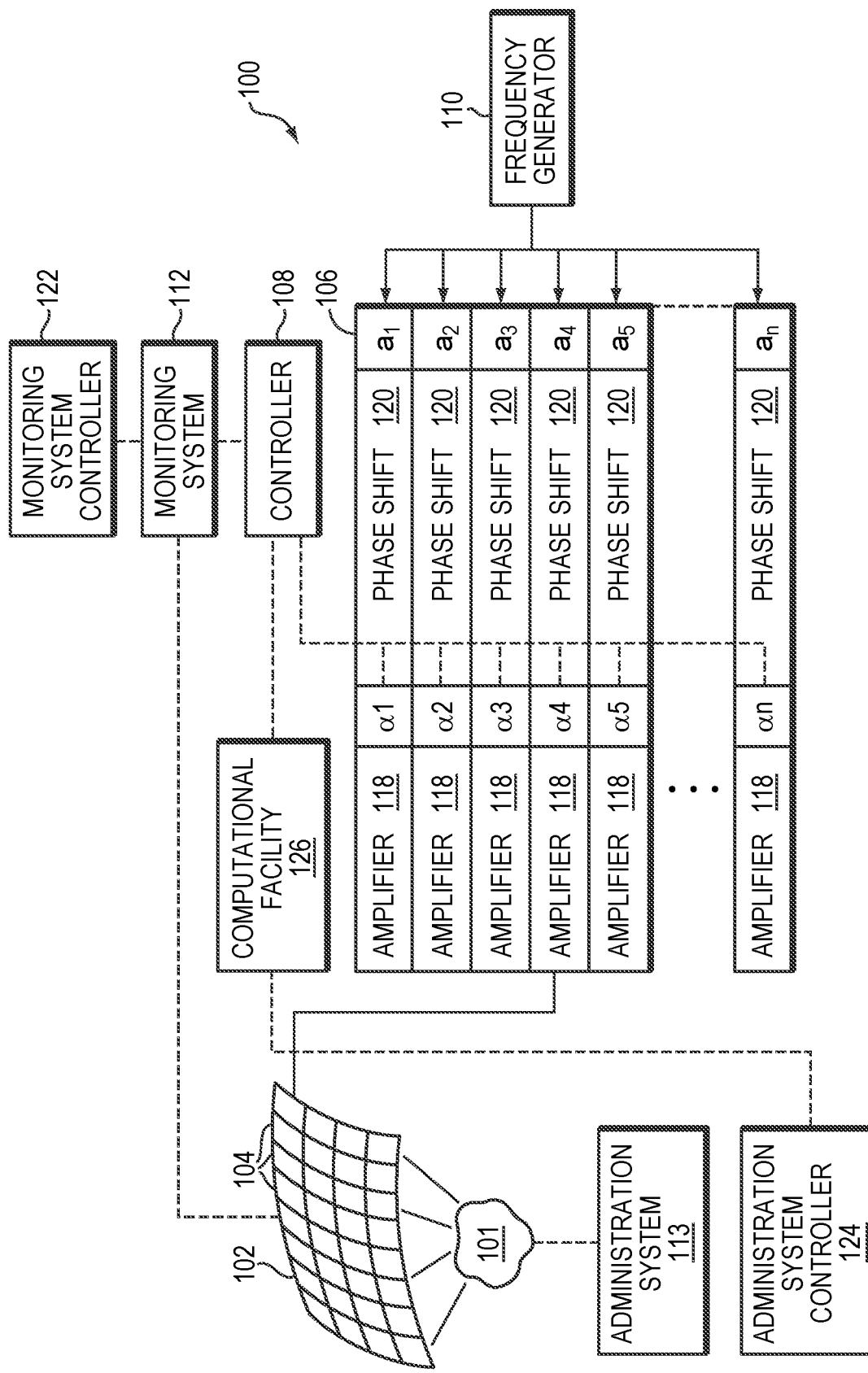
FIG. 1 illustrates a microbubble-mediated focused ultrasound system in accordance with various embodiments.

FIG. 1 illustrates an exemplary ultrasound system 100 for generating and delivering a focused acoustic energy beam to a target region 101 within a patient's body. The illustrated system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes a monitoring system 112 for detecting information about the patient and an administration system 113 for introducing an exogenous agent and microbubbles into the patient's body as further described below. The monitoring system 112 and administration system 113 may be operated using the same controller 108 that facilitates the transducer operation; alternatively, they may be separately controlled by two separate controllers 122, 124, respectively. The controllers 108, 122, 124 may intercommunicate.

The array 102 may have a curved (e.g., spherical or parabolic) or other contoured shape suitable for placement on the surface of the patient's body, or may include one or more planar or otherwise shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezocomposite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radio frequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through the intervening tissue located between the transducer elements 104 and the target region onto the target region 101, and account for wave distortions induced in the intervening tissue. The amplification factors and phase shifts are computed using the controller 108, which may provide the computational functions through software, hardware, firmware, hardwiring, or any combination thereof. In various embodiments, the controller 108 utilizes a general-purpose or special-purpose digital data processor programmed with software in a conventional manner, and without undue experimentation, in order to determine the phase shifts and amplification factors necessary to obtain a desired focus or any other desired spatial field patterns. The determined phase shifts and amplification factors together with other acoustic parameter(s)

may then be included in a treatment plan for treating the target region 101 as further described below.

Figure 2A:
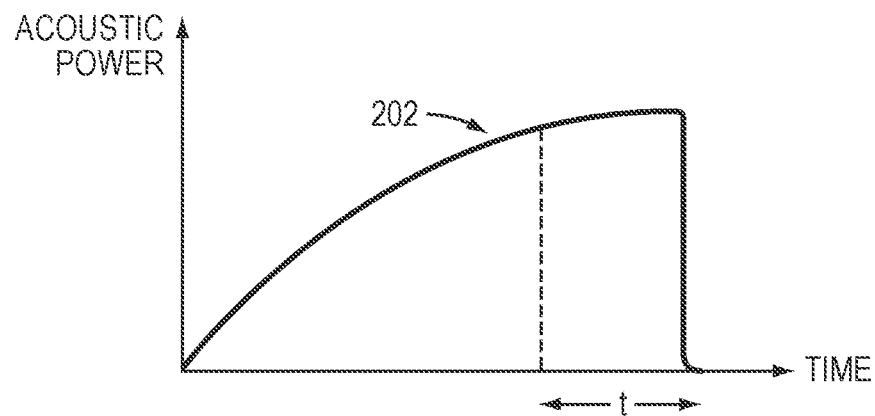
FIG. 2A depicts an exemplary acoustic power profile of an ultrasound transducer specified in a treatment plan in accordance with various embodiments of the present invention.

In certain embodiments, the monitoring system 112 includes an imager, such as a magnetic resonance imaging (MRI) device, a computer tomography (CT) device, a positron emission tomography (PET) device, a single-photon emission computed tomography (SPECT) device, or an ultrasonography device, for determining characteristics (e.g., the type, property, structure, size, location, shape, temperature, etc.) of the tissue at the target region 101 and/or the non-target region. The treatment plan may include one or more acoustic parameters associated with the transducer 102. For example, referring to FIG. 2A, the treatment plan may specify an acoustic power profile 202 over time. In one embodiment, the rise of the power is steeper at the beginning of treatment as the power absorbed by the target region 101 is far below the desired level and the tissue responses are typically not instantaneous to the applied acoustic energy. As the treatment proceeds and the acoustic power approaches the desired power level, the rise of the acoustic power may taper off—i.e., increase at a slower rate to avoid damage to the target and/or non-target (hereafter "target/non-target") regions. In addition, based on the tissue characteristics (e.g., size, shape and/or location) of the target/non-target regions, the application time, t, of the acoustic power that is sufficiently to disrupt the target tissue may be computed. Once the requirement of the application time is met, the ultrasound sonications may be turned off or shifted to another target region for treatment.

To determine a suitable acoustic power profile for treatment, in various embodiments, a tissue model is used to characterize the material properties of the target and/or non-target tissue, such as their heat sensitivities and/or tolerable thermal energies. The treatment plan then specifies one or more therapeutic objectives including a disruption level at the target region 101 and/or a maximum tolerable temperature, an acoustic energy and/or an acoustic response (e.g. a cavitation dose) at the non-target region. A physical model that simulates ultrasound field aberrations resulting from, for example, beams traversing inhomogeneous intervening tissue located between the transducer 102 and the target tissue 101, transducer geometry and/or acoustic field design (e.g., for refocusing purposes) can be used to inversely compute the required acoustic power and/or other parameter values (e.g., amplitudes, frequencies, phases, directions and/or activation time associated with the transducer elements, or time intervals between consecutive series of sonications) associated with the transducer elements 104 based on the location and disruption temperature of the target region 101 and/or the maximum tolerable temperature at the non-target region. These ultrasound parameter values may be included in the treatment plan as well. Further details about establishing the tissue model and physical model are provided, for example, in International Application No. PCT/IB2017/001689 (filed on Dec. 13, 2017), International Patent Publication No. WO 2018/130867, and U.S. Patent Publication No. 2015/0359603, the entire disclosures of which are hereby incorporated herein by reference. In addition, approaches to computationally generating a treatment plan using the tissue model and physical model are provided in International Application No. PCT/IB2018/000834 (filed on Jun. 29, 2018), the entire disclosure of which is hereby incorporated herein by reference.

Referring again to FIG. 1, additionally or alternatively, the monitoring system 112 may include one or more biosensors for measuring one or more physiological parameters (e.g., blood pressure, blood circulation rate, blood perfusion rate, and/or heart rate) of the patient. The monitoring system 112 may be controlled by the ultrasound controller 108, or alternatively, a separate controller 122. For example, the monitoring system 112 may be a standard heart rate measurement system with an internal controller 122 that is operated manually. The controller 122 may be in communication with the ultrasound controller 108 and/or a computational facility 126 so as to provide the measured physiological parameter(s) thereto prior to and/or during the ultrasound procedure. The computational facility 126 facilitates treatment planning and adjustment and may take the measured physiological parameter(s) into account when determining and/or modifying the treatment plan as further described below.

Typically, the treatment plan specifies the therapeutic objective(s) (e.g., ablation of a target) and a sequence of actions (e.g., administration of the therapeutic agent(s) and/or microbubbles and sonication) with associated parameters for attaining the objective(s). It should be understood that modifying the treatment plan, as described herein, need not involve revision of the entire plan, but may instead alter one aspect or parameter of it. For example, if a signal detected by the monitoring system 112 is interpreted as indicating excessive cavitation, the computational facility may merely reduce the administration rate of the exogenous agent (and thereby the microbubbles) or adjust the sonication amplitude to remain within clinically safe treatment parameters. Alternatively, it may revise more related parameters, one or more objectives of the treatment plan, or the entire plan. Any of these changes or revisions is understood herein as modifying or adjusting the treatment plan.

The treatment plan may itself be responsive to sensed physiological parameters. For example, based on a measured blood circulation rate, the treatment plan may specify characteristics (e.g., a volume and/or a concentration profile) of the exogenous agent carrying microbubbles for treatment—a higher blood circulation rate may require a larger volume/concentration of the exogenous agent in order to initiate and/or maintain the treatment. Typically, the microbubbles are homogeneously suspended in the exogenous agent; therefore, controlling the characteristics (e.g., volume or concentration) of the exogenous agent may directly determine (and vary) the characteristics of the microbubbles. In addition, the measured physiological parameter(s) may determine the acoustic parameters associated, in the treatment plan, with the transducer 102. For example, a higher blood perfusion rate may result in a faster heat transfer from the transducer 102 to the target region 101, thereby reducing the required sonication time. As a result, the treatment plan may specify a relatively shorter sonication time when a relatively higher bold perfusion rate is detected. Again, measurements of the physiological parameter(s) may be performed using any suitable biosensor(s) that can be attached to or implanted in the patient's body and may be acquired off-the-shelf.

In some embodiments, the treatment plan specifies a chemical property of the microbubbles that affects microbubble cavitation effects on the target tissue. The chemical property of the microbubbles may be determined by, for example, the type of gas encapsulated, the molecular weight or composition of the shell material, and/or the manufacturing approach; accordingly, these parameters may be included in the treatment plan. In addition, the treatment plan may specify a size distribution of the microbubbles in the exogenous agent, as the size of the microbubbles controls the microbubble resonance frequency in response to the ultrasound sonications.

Figure 2B:
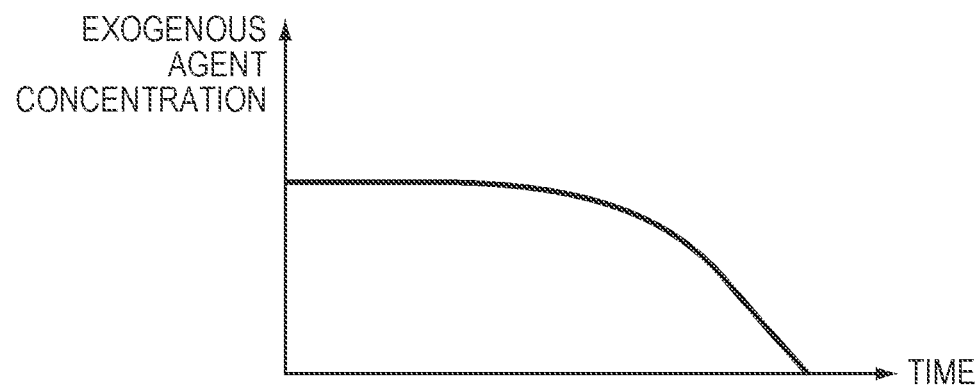
FIGS. 2B and 2C depict exemplary administration profiles of an exogenous agent carrying microbubbles specified in a treatment plan in accordance with various embodiments of the present invention.
Figure 2C:
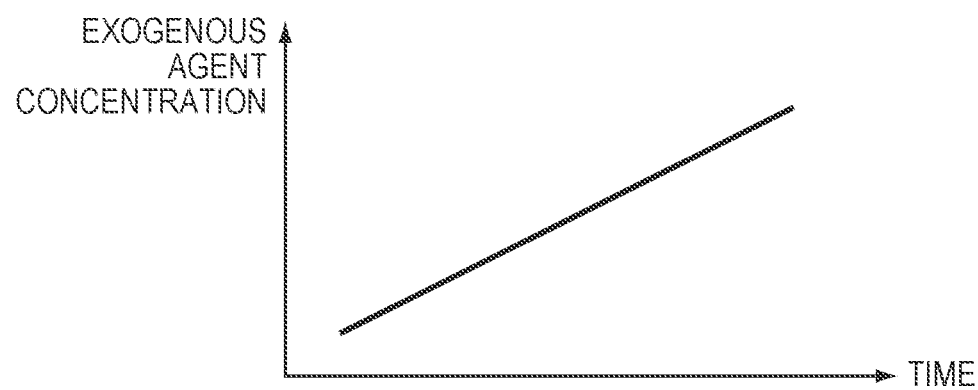

Generally, the volume of injected exogenous agent in a treatment is limited to prevent hazards resulting from the procedure (e.g. excessive gas in the patient's circulatory system). With reference to FIG. 2B, to effectively use the limited amount of exogenous agent, in various embodiments, a relatively higher concentration of the exogenous agent is injected to initiate the microbubble-enhanced ultrasound procedure at the beginning of treatment; a relatively lower injection rate is used for the purpose of maintaining sufficient microbubble cavitation during treatment. In other embodiments, with reference to FIG. 2C, it is desired to increase the concentration of the exogenous agent as the treatment proceeds (so as to reduce the sonication power for safety purposes); in this case, the concentration of the exogenous agent may be continuously or discretely increased over time. Regardless of which administration profile is used, the acoustic power profile and tissue characteristics of the target/non-target region may be taken into account to avoid undesired damage to the target and/or non-target tissues when creating the treatment plan.

In various embodiments, the ultrasound procedure is performed in combination with other therapeutic methods, such as radiation therapy or targeted drug delivery. For example, the ultrasound-induced microbubble oscillation/cavitation may disrupt vascular tissue in the target region 101; this allows the radiation dose in radiation therapy to be significantly reduced while still achieving the desired treatment efficacy. In another treatment scenario, ultrasound-induced microbubble oscillation/cavitation may increase the tissue permeability at the target region (e.g., opening the BBB); this allows a higher dose of therapeutic agent to reach the target tissue 101, thereby enhancing the therapeutic effect. Accordingly, the treatment plan may specify the radiation dose and/or characteristics (e.g., a type, a dose, a concentration profile, a temperature, or an administration profile) of one or more therapeutic agents for target treatment. Approaches to utilizing microbubble oscillation/cavitation to reduce the radiation dose in radiation therapy and increase tissue permeability at the target region 101 are provided, for example, in U.S. patent application Ser. No. 15/637,163 (filed on Jun. 29, 2017) and in International Application No. PCT/IB2018/000811 (filed on Jun. 29, 2018), respectively, the contents of which are incorporated herein by reference.

Figure 2D:
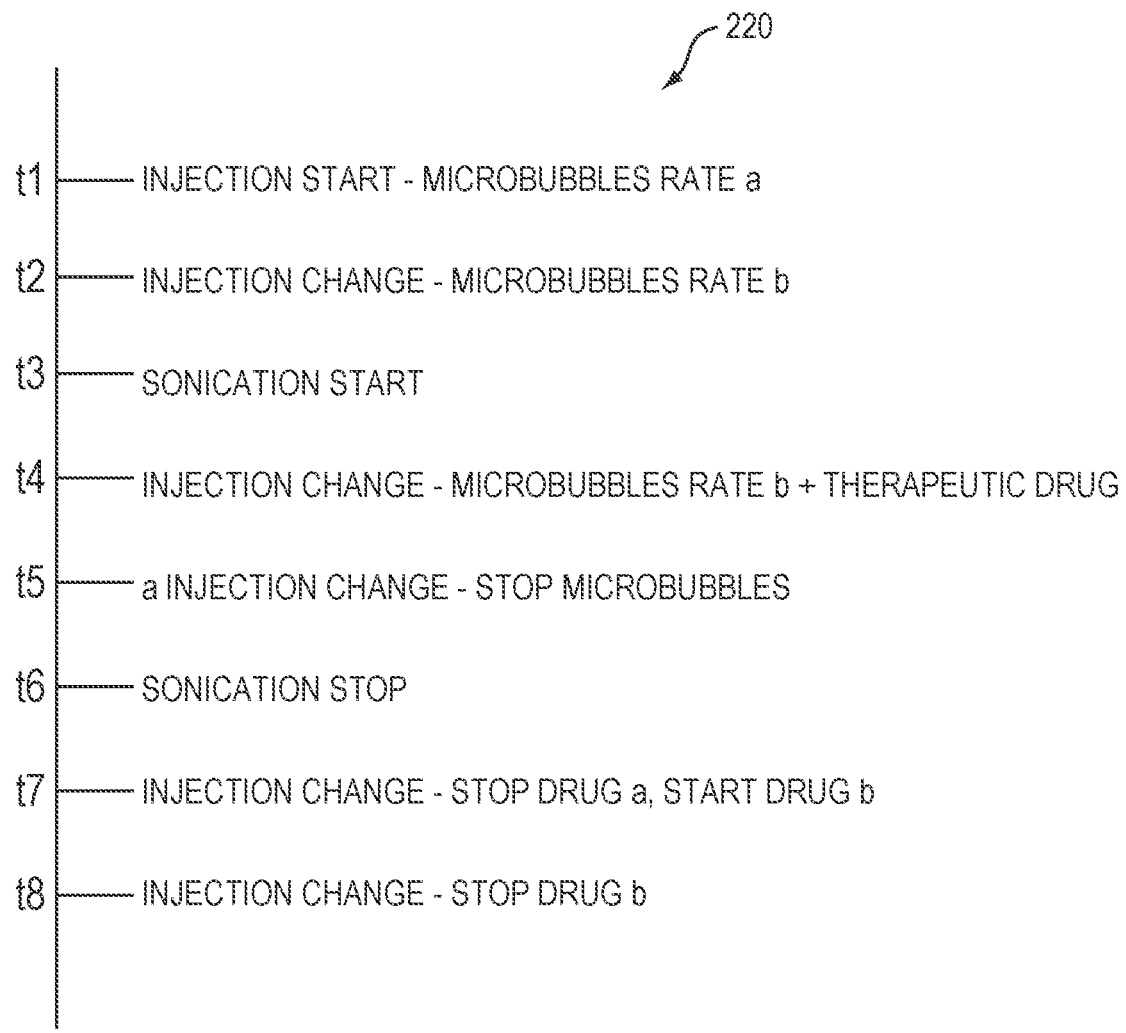
FIG. 2D depicts an exemplary treatment plan specifying a sequence of operations of an ultrasound transducer and an administration system in accordance with various embodiments of the present invention.

For example, the treatment plan may specify the administration timing of multiple therapeutic agents into the target 101. The sequentially or substantially simultaneously introduced therapeutic agents may achieve a desired treatment effect at the target 101. FIG. 2D depicts an exemplary treatment plan 210 specifying operations of the transducer 102 and administration system 113 for applying sonications and/or introducing the therapeutic agent(s) and/or exogenous agent to the target 101. As shown, the treatment plan specifies that at time $t_1$, the administration system 113 commences microbubble injection at a rate R, where R=a. At time $t_2$, the controller 108/124 causes the administration system 113 to introduce the microbubbles at a different rate R=b. Subsequently, at time $t_3$, the controller 108 causes the transducer 102 to transmit sonications to the target region 101 to disrupt the tissue therein. At time $t_4$, the microbubbles and sonications produce a treatment effect (e.g., disrupting at least a portion of the target tissue) such that a type "a" therapeutic agent is suitable to be applied to treat the target 101. Accordingly, the treatment plan may specify commencing administration of the type "a" therapeutic agent and further administration of the microbubbles (at the injection rate of R=b) at time $t_4$. In various embodiments, once a desired degree of tissue disruption in the target region 101 has been achieved, the microbubble injection is terminated at time $t_5$; and subsequently, the sonications are suspended at time $t_6$. In the illustrated treatment plan, multiple therapeutic agents are used to the target 101, and the treatment plan specifies terminating administration of the type "a" therapeutic agent and, instead, injecting a new therapeutic agent (e.g., type "b") in the target 101 at time $t_7$. Finally, when the desired therapeutic objectives are achieved, injection of the type "b" therapeutic agent is terminated at time $t_8$.

It should be noted that the treatment plan illustrated in FIG. 2D represents an exemplary embodiment only; more generally, a treatment plan may include various operations of the transducer 102, administration system 113 and/or other treatment apparatus (e.g., a radiation device) that are suitable for treating the target region 101 and therefore are within the scope of the present invention. In addition, the administration system 113 may be controlled by the ultrasound controller 108, the monitoring system controller 122, or a separate controller 124. The controller 124 may be in communication with the ultrasound controller 108, the monitoring-system controller 122, and/or the computational facility 126, and operate the administration system 113 based on signals received therefrom so as to achieve a desired treatment effect at the target region 101.

Figure 3A:
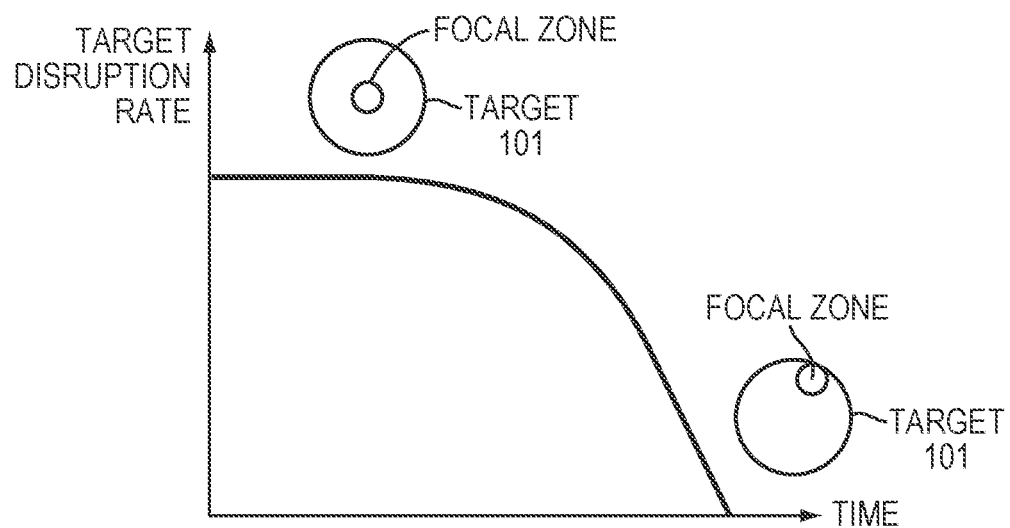
FIGS. 3A and 3B illustrate exemplary tissue-disruption rate profiles of the target tissue specified in a treatment plan in accordance with various embodiments of the present invention.
Figure 3B:
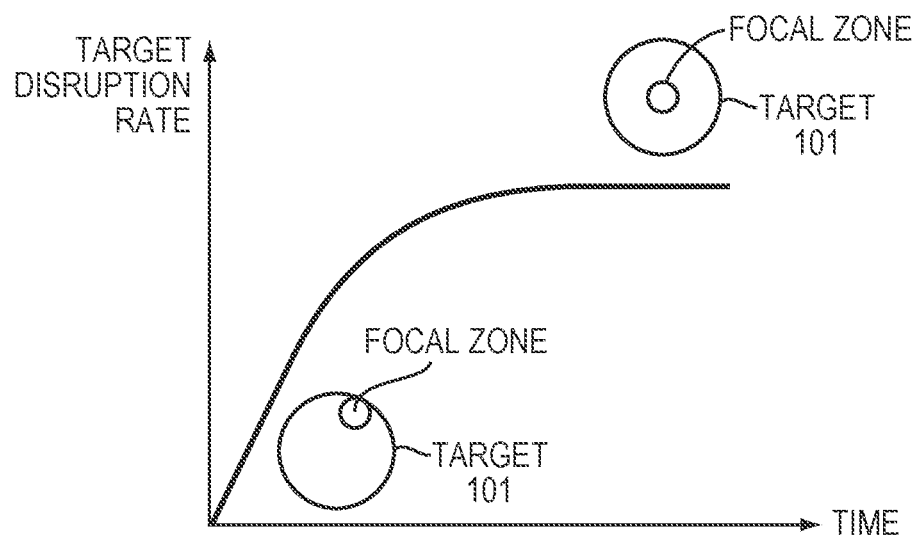

The treatment plan typically reflects a trade-off between the treatment rate, treatment time, and risk to non-target tissues. Although a higher treatment rate may reduce treatment time and increase treatment efficiency, the risk of damage to non-target tissue may increase and thereby create a safety hazard. Conversely, a slower rate may decrease the risk of damaging the non-target tissue, but may reduce the treatment efficiency and prolong the treatment time, which may itself ultimately create a safety hazard. Therefore, in some embodiments, the treatment plan may include a tissue-disruption rate profile of the target tissue over time. For example, referring to FIG. 3A, at the beginning of treatment, the ultrasound focal zone (and thereby the tissue region that is disrupted) may be significantly smaller than the entire target region 101; in such circumstances, the risk of damaging the tissue surrounding the target region 101 is small, so a high disruption rate may be preferred to increase treatment efficiency. As treatment proceeds, the volume of disrupted tissue increases and the distance between the focal zone and non-target tissue diminishes, and a point may be reached where it is desirable to reduce the disruption rate so as to avoid damaging the non-target tissue. Alternatively, with reference to FIG. 3B, the treatment may begin by focusing the ultrasound beam near the boundary between the target and non-target regions. Because the focal zone is near the boundary, it may be preferable to start with a small disruption rate that gradually increases as the focal zone moves into the center of the target region 101 and away from the boundary.

Figure 4:
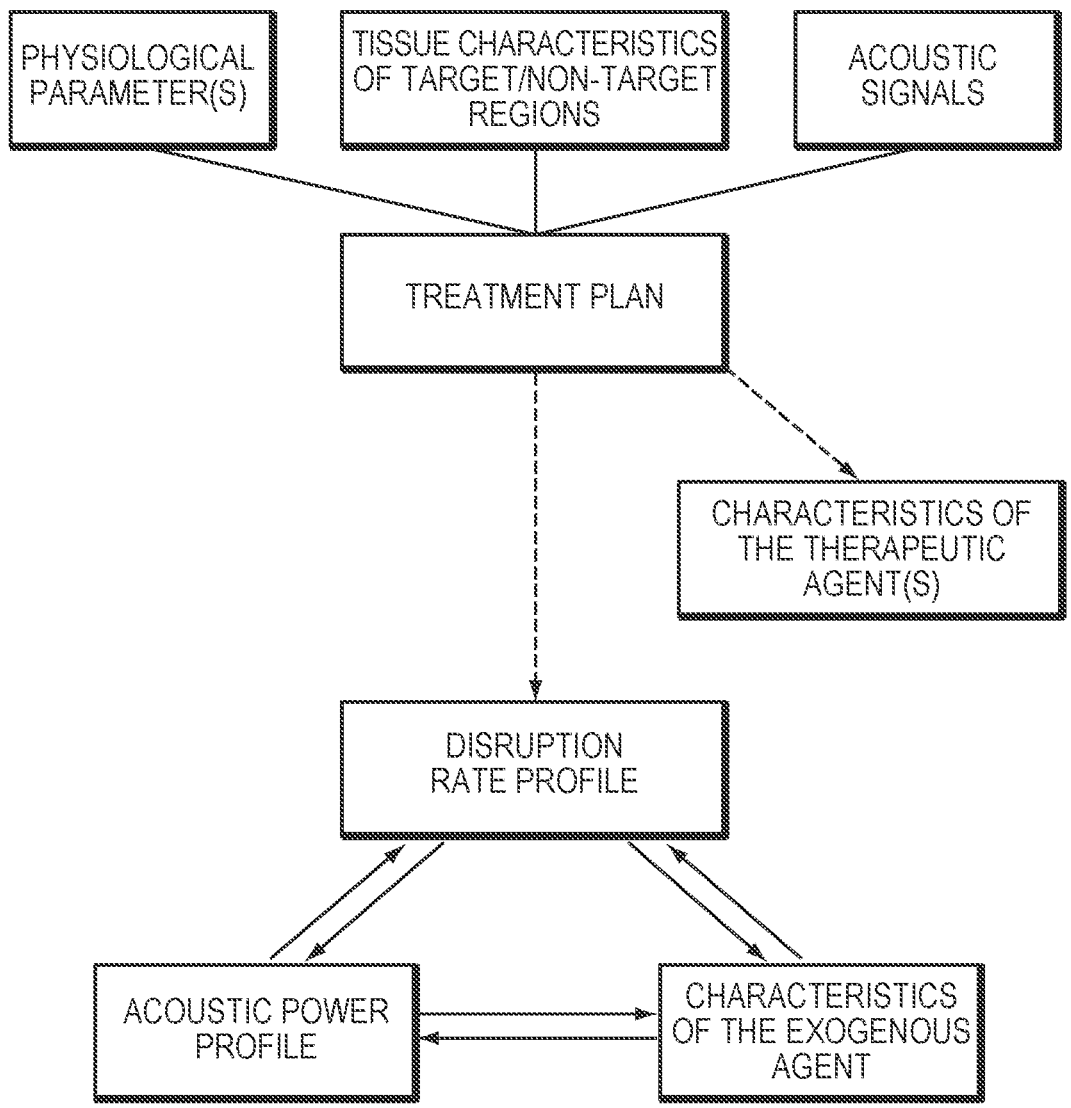
FIG. 4 illustrates various factors contributing to a treatment plan and interrelationships between various parameters specified by the treatment plan in accordance with various embodiments of the present invention.

Achieving a desired disruption rate profile may involve adjusting the characteristics of the exogenous agent and/or acoustic power profile. For example, an injection rate profile of the exogenous agent over time may be created based on the desired disruption rate profile. Because the microbubbles in the exogenous agent enhance the effect of the ultrasound, the injection rate profile of the exogenous agent affects the amount of acoustic energy that must be applied to achieve the desired therapeutic effect. FIG. 4 illustrates various factors that may contribute to the treatment plan and the interrelationship between the various parameters specified by the treatment plan. As depicted, the treatment plan may be determined based on physiological parameter(s) measured using biosensors and/or tissue characteristics of target/non-target regions acquired using an imager. The treatment plan may include the disruption rate profile of the target tissue, characteristics (e.g., the type, dose, concentration profile, or administration profile) of the therapeutic agent(s) and/or the exogenous agent carrying microbubbles, and/or acoustic power profile of the ultrasound system. Generally, the disruption rate profile dictates the characteristics of the exogenous agent and the acoustic power profile of the ultrasound system, as these parameters are interrelated. But this is not necessarily the case. For example, the characteristics of the exogenous agent may be determined based on the physiological parameters only and the tissue disruption rate profile may be determined based on the tissue characteristics of the target/non-target regions only. The determined tissue disruption rate profile and characteristics of the exogenous agent may then, in turn, determine the acoustic power profile. Alternatively, the tissue disruption rate profile and acoustic power profile may define the characteristics of the exogenous agent to be injected. For example, the optimal concentration of exogenous agent may be selected based on a desired acoustic power—a higher concentration of exogenous agent permits use of less acoustic power to achieve microbubble cavitation. When, for example, the tissue surrounding the target BBB region is sensitive to acoustic energy, low-power sonications may be employed to avoid damage to the surrounding tissue. In this case, the concentration of the exogenous agent may be increased to ensure that the low-power sonications still induce sufficient cavitation events to achieve the objectives of the treatment plan. Systems and methods for adjusting the characteristics of the exogenous agent and/or microbubbles contained therein are described, for example, in International Patent Application No. PCT/IB2018/000841 (filed on Jun. 29, 2018) and International Patent Application entitled "Controlling Delivery of Therapeutic Agent in Microbubble-Enhanced Ultrasound Procedures" filed on even date herewith, the entire disclosures of which are hereby incorporated by reference.

During treatment, the transducer 102 and administration system 113 may be operated based on the treatment plan. In addition, the monitoring system 112 may in real-time detect the characteristics of the exogenous agent and/or therapeutic agent(s), acoustic signals and/or tissue characteristics of the target region 101, and provide the detected characteristics/signals to the computational facility 126. Based on the provided information, the computational facility 126 may adjust the treatment plan and cause the transducer 102 and/or administration system 113 to be driven in accordance with the adjusted treatment plan so as to ensure treatment efficiency and safety. The adjustment may include, for example, varying the concentration profile of the exogenous agent and/or therapeutic agent(s), changing the type of the therapeutic agent(s), changing the size distribution of the microbubbles in the exogenous agent, adjusting the acoustic power level, etc. Accordingly, various embodiments of the present invention provide a closed-loop, real-time feedback system that offers information about the target/non-target region and/or exogenous agent so as to allow a treatment adjustment/optimization.

In various embodiments, the monitoring system 112 includes one or more acoustic-signal detectors for measuring acoustic signals from the target/non-target regions and feeding it back to the computational facility 126 for adjusting the treatment plan. The measured acoustic signals may indicate the microbubble response to the sonications and/or the focusing properties at the target and/or non-target regions. For example, the amplitude of acoustic reflections from a region of tissue generally corresponds to the volume or concentration of the exogenous agent in this region. Accordingly, in one embodiment, the relationship between the reflection amplitude and the volume/concentration of the exogenous agent is established prior to treatment (as described below). This relationship may be exploited during treatment so as to adjust the administering volume or concentration of the exogenous agent from the administration system 113 and/or the transducer parameter values for achieving the desired treatment objective(s). Approaches to using detected acoustic signals to measure the microbubble response and/or the focusing properties at the target region are provided, for example, in International Patent Applications entitled "Adaptive, Closed-Loop Ultrasound Therapy" and "Controlling Delivery of Therapeutic Agent in Microbubble-Enhanced Ultrasound Procedures" filed on even date herewith, the entire disclosures of which are hereby incorporated by reference. Alternatively, the transducer elements 104 may possess both transmit and receive capabilities. Thus, at least some of the transducer elements may be configured to measure acoustic signals from the target/non-target region. Approaches to configuring the transducer elements 104 for detecting the reflected signals are provided, for example, in the U.S. Patent Application No. 62/861,282, the contents of which are incorporated herein by reference.

The relationship between the acoustic reflections and the volume/concentration of the exogenous agent may be established based on measurements from previous treatment(s) on the same or a different patient, or averaged across patients. In one embodiment, the relationship is established at the beginning of the treatment. For example, when the exogenous agent is injected in accordance with an administration profile specified by the treatment plan, a slightly defocused acoustic beam (e.g., 5% or 10% of the distance behind the surface of the target region 101) may be utilized to measure the reflection signals. The defocused beam allows information about the exogenous agent (e.g., the microbubble concentration) to be measured without inducing microbubble cavitation. In addition, as the volume/concentration of microbubbles varies during and after administration of the exogenous agent, the measured ultrasound reflections therefrom may change. Once related to the volume/concentration of microbubbles, the reflection measurements can serve as a proxy for this parameter in the treatment plan. (Because an exogenous agent will contain a known concentration of microbubbles, references are interchangeably made to the volume/concentration of exogenous agent or microbubbles.)

Figure 5A:
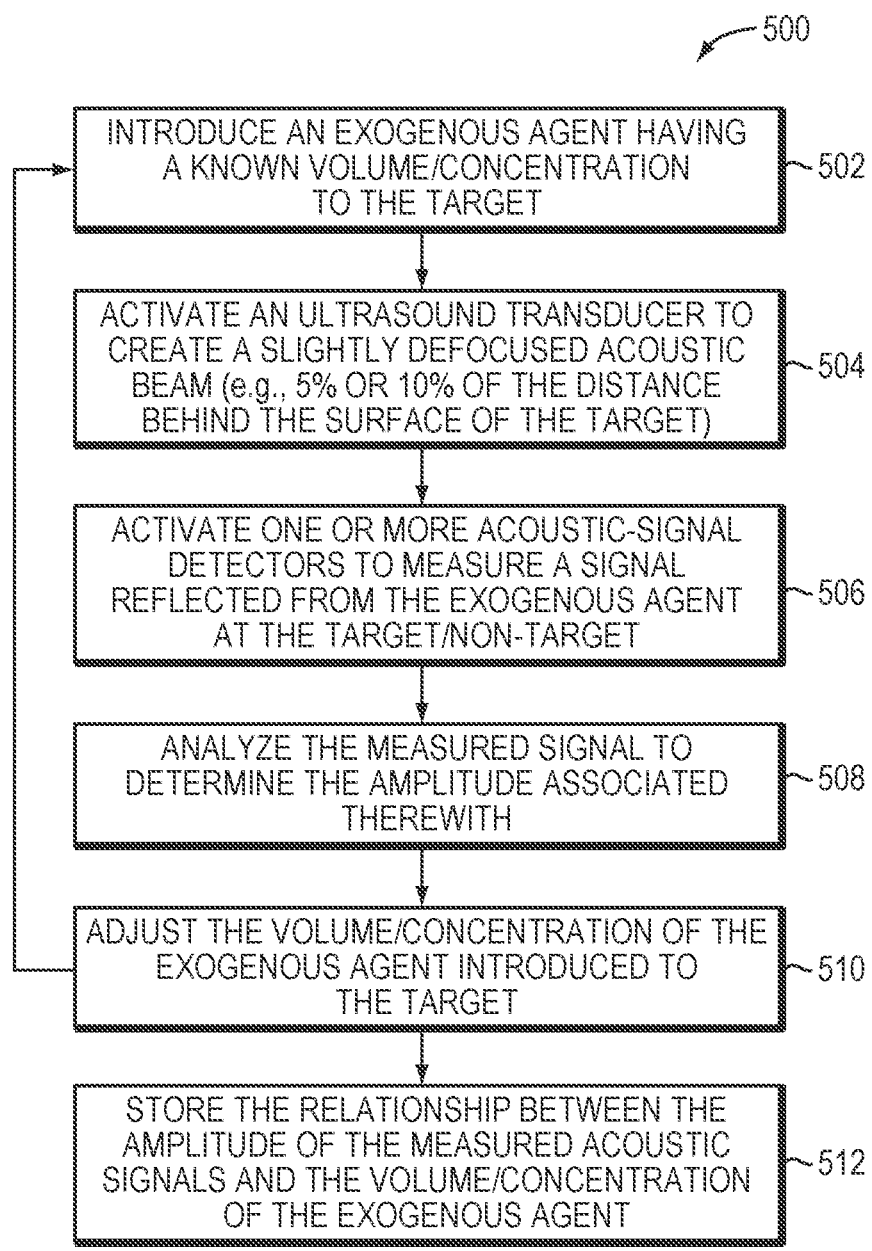
FIG. 5A is a flow chart illustrating an approach for establishing a relationship between an amplitude of measured acoustic signals and a volume/concentration of an exogenous agent in accordance with various embodiments of the present invention.
Figure 5B:
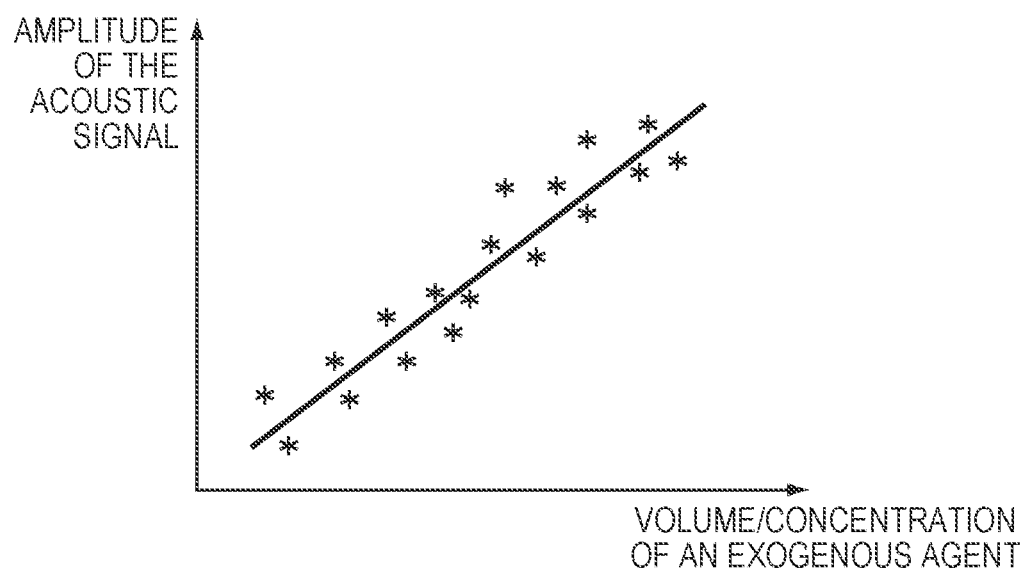
FIG. 5B depicts an exemplary relationship between an amplitude of measured acoustic signals and a volume/concentration of an exogenous agent in accordance with various embodiments of the present invention.

FIG. 5A illustrates an exemplary approach 500 for establishing a relationship between the amplitude of the measured acoustic signals and the volume/concentration of the exogenous agent in accordance herewith. In a first step 502, the exogenous agent having a known volume and concentration of microbubbles is first introduced to the target region 101. In a second step 504, the ultrasound transducer 102 is activated to create an acoustic beam. Optionally, the acoustic beam may be slightly defocused (e.g., 5% or 10% of the distance behind the surface of the target region 101). In a third step 506, the acoustic-signal detector(s) may be activated to detect a signal reflected from the exogenous agent at the target region 101. In a fourth step 508, the measured signal is analyzed by the controller 108/122/124 or the computational facility 126 to determine the amplitude associated therewith. In a fifth step 510, the volume/concentration of the exogenous agent introduced to the target region 101 is then adjusted. The transducer elements 104 may then be activated to create another acoustic beam (which may or may not slightly defocused off the target), and the acoustic-signal detector(s) may measure the signals from the newly administrated exogenous agent. In various embodiments, steps 504-510 are repeated until sufficient data has been acquired to reliably establish the relationship between the amplitude of the measured acoustic signals and the volume/concentration of the exogenous agent (as depicted in FIG. 5B). The relationship may then be stored in memory accessible to the computational facility 126 during treatment (in step 512).

In addition, in some embodiments, an elapsed time, Δt, between of an ultrasound wave from the transducer 102 and the detection of a reflection signal from cavitation is measured using the acoustic-signal detector(s). Based on the measured elapsed time and the speed of sound in the tissue medium, the distance between the transducer 102 and the cavitation event can be computed. This approach may be used to verify whether the location of the cavitation coincides with the target region 101. Approaches to computing locations of microbubble cavitation events are provided in U.S. Patent Publication No. 2018/0206816, the entire disclosure of which is hereby incorporated herein by reference.

Generally, a larger amount of microbubble cavitation may result in a larger amount (e.g., amplitude) of acoustic emissions therefrom; therefore, by detecting the amount (e.g., the amplitude) of acoustic emissions from the microbubbles, the amount of cavitation events can be determined. In various embodiments, this information is combined with the determined location of the microbubble cavitation as described above so as to determine the amount of cavitation at the target region 101 and/or non-target region. This approach may advantageously provide real-time monitoring of the amount of microbubble cavitation in the target/non-target region during treatment by inferring it from the detected reflections. Again, this approach may involve use of a relationship between the value (e.g., the power or amplitude) of the detected acoustic signals and the amount of cavitation events at the target region, which, again, can be straightforwardly established prior to treatment (as described in FIGS. 5A and 5B).

Further, the detected acoustic emissions from the microbubbles may indicate the type of cavitation thereof. This is feasible because different types of cavitation typically have different spectral signatures. For example, at a relatively low acoustic power (e.g., 1-2 Watts above the microbubble-generation threshold), the generated microbubbles undergo oscillation with compression and rarefaction that are equal in magnitude and thus the microbubbles generally remain unruptured (i.e., a "stable cavitation"). The acoustic response of microbubbles is linear at this low acoustic power and the frequency of ultrasound emitted from the microbubbles is the same as or a harmonic of that of the incident ultrasound waves (i.e., the fundamental frequency or a base harmonic frequency). At a higher acoustic power (e.g., more than 10 Watts above the microbubble-generation threshold), the generated microbubbles undergo rarefaction that is greater than compression, which may cause cavitation and a nonlinear acoustic response of the microbubbles. The acoustic signals returned from cavitation events may include frequencies at the fundamental frequency and/or a harmonic, ultra-harmonic, and/or sub-harmonic of the fundamental frequency. Accordingly, by detecting and analyzing the acoustic signals emitted from the microbubbles, the presence and/or type of cavitation induced in tissue during an ultrasound procedure can be determined. This approach may require a mapping between various types of cavitation events and their spectral signatures, which, again, can be straightforwardly established prior to treatment as further described below. As used herein, the term "fundamental" frequency or "base harmonic" frequency, $f_0$, refers to the frequency (or temporally varying frequency) of the ultrasound waves/pulses emitted from the transducer array 102; the term "harmonic" refers to an integer number of the fundamental frequency (e.g., $2f_0$, $3f_0$, $4f_0$, etc.); the term "ultra-harmonic" refers to a fractional frequency between two nonzero integer harmonics (e.g., $3f_0/2$, $5f_0/4$, etc.); and the term "sub-harmonic" refers to a fractional number between the fundamental frequency and the first harmonic (e.g., $f_0/2$, $f_0/3$, $f_0/4$, etc.).

Figure 6:
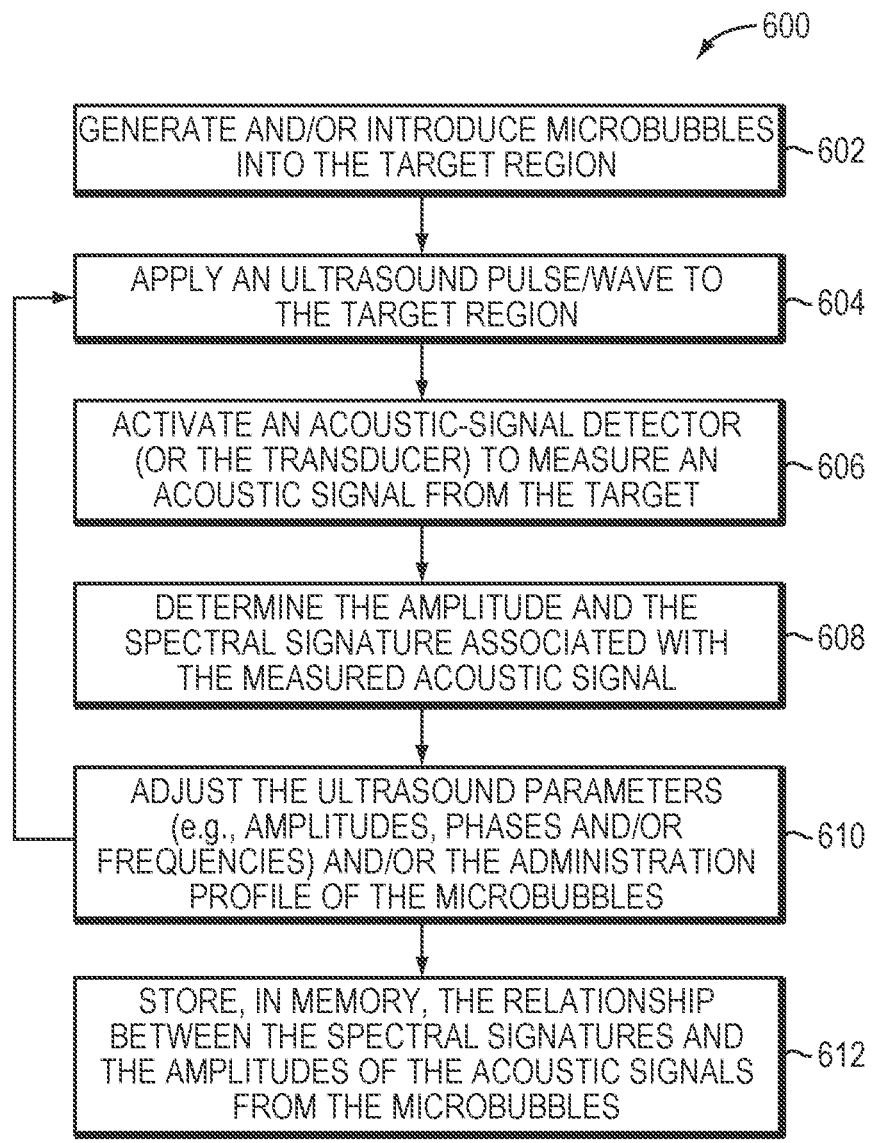
FIG. 6 is a flow chart illustrating an approach for establishing a relationship between a spectral signature of measured acoustic signals from the target region and an amount of cavitation events at the target region in accordance with various embodiments of the present invention.

FIG. 6 depicts an exemplary approach 600 for establishing the relationship between the spectral signatures and their corresponding types of cavitation in accordance herewith. In a first step 602, the microbubbles may be generated within and/or introduced into the target region 101. In a second step 604, the transducer elements 104 may apply an ultrasound pulse/wave to the target region 101. The parameter values (e.g., amplitudes, phases, or frequencies) associated with the transducer elements 104 may be estimated empirically and/or using the physical model as described above so as to generate a focus at the target region. In a third step 606, upon application of the ultrasound wave, the acoustic-signal detector(s) (or, in some embodiments, the transducer elements 104) may be activated to measure an acoustic signal from the target. In a fourth step 608, the measured acoustic signal is then transmitted to the controller 108 and/or computational facility 126 for determining the amplitude and the spectral signature associated therewith. In a fifth step 610, the ultrasound parameters (e.g., amplitudes, phases, or frequencies) and/or the administration profile of the microbubbles can then be adjusted, and the acoustic signal in response to the adjusted ultrasound parameter values/administration profile are measured. Step 604-610 may be repeated until sufficient data has been acquired to reliably establish the relationship between the spectral signatures and the amplitudes of the acoustic signals from the microbubbles. Again, the established relationship may then be stored in memory accessible to the controller 108 and/or computational facility 126 for retrieval during treatment (in step 612).

Figure 7A:
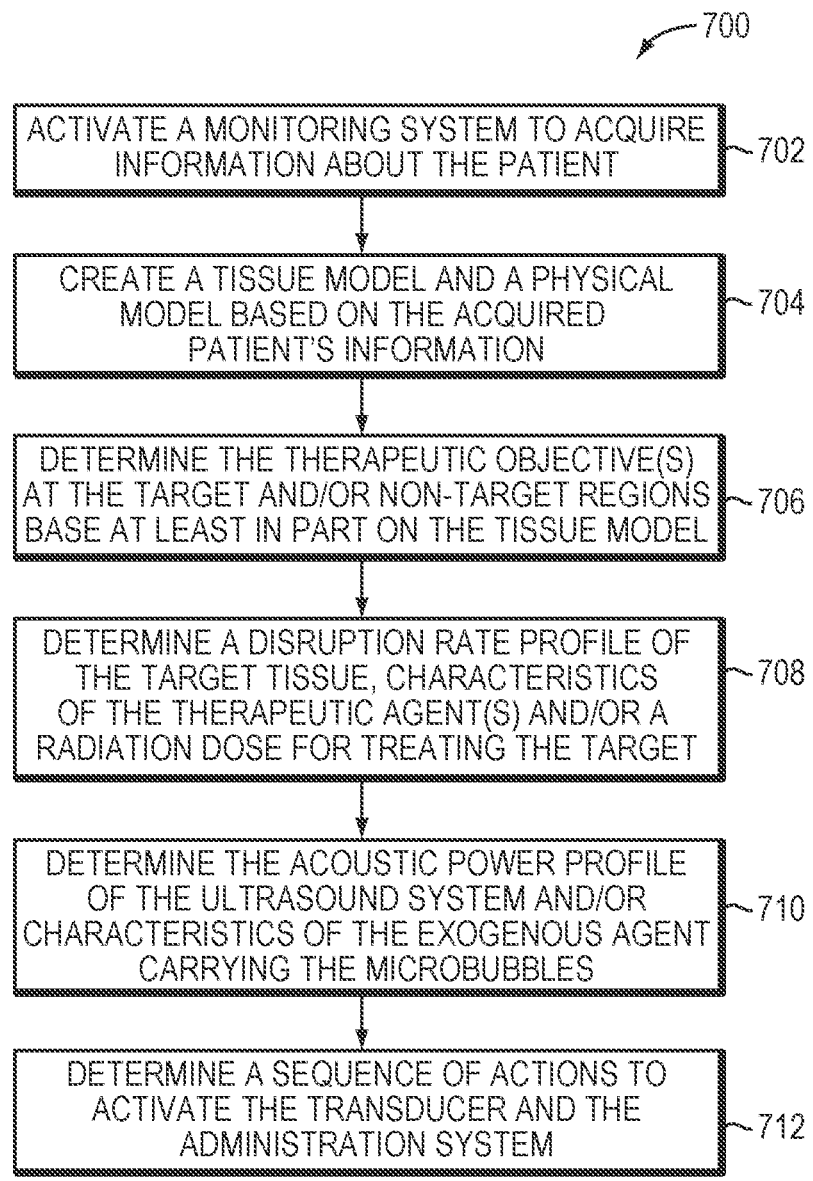
FIG. 7A is a flow chart illustrating an approach for creating a treatment plan for a microbubble-mediated ultrasound procedure in accordance with various embodiments of the present invention.

FIG. 7A illustrates an exemplary approach 700 for creating a treatment plan for a microbubble-mediated ultrasound procedure in accordance herewith. In various embodiments, preparatory steps 702-712 are performed for creating the treatment plan prior to treatment. In a first preparatory step 702, the monitoring system 112 is activated to acquire information about the patient. For example, the monitoring system 112 may include an imager (e.g., MRI apparatus) for acquiring images of the target and/or non-target tissue. The acquired images are then analyzed by a controller that implements conventional image-analysis software to determine the location and/or anatomic characteristics (e.g., type, property, structure, thickness, density, etc.) of the target/non-target tissue. Additionally or alternatively, the monitoring system 112 may include a biosensor for measuring a physiological parameter (e.g., the blood pressure, blood circulation rate, blood perfusion rate, and/or heart rate) of the patient. In a second preparatory step 704, based on the acquired patient's information, a tissue model characterizing the material properties (e.g., heat sensitivity, tolerable thermal energy, energy absorption of the tissue at the employed frequency and/or the speed of sound) of the target and/or non-target tissue and a physical model that simulates ultrasound field aberrations resulting from, for example, beams traversing inhomogeneous intervening tissue, transducer geometry and/or acoustic field design (e.g., for refocusing purposes) can be created. In a third step 706, the computational facility 126 may determine the therapeutic objective(s) including a disruption level at the target region 101 and/or a maximum tolerable temperature, an acoustic energy and/or an acoustic response (e.g. a cavitation dose) at the non-target region based on the tissue model. In a fourth step 708, based on the determined therapeutic objective(s), the computational facility 126 may then determine a disruption rate profile of the target tissue, characteristics (e.g., a type, a dose, a concentration profile, a temperature, or an administration profile) of the therapeutic agent(s) and/or a radiation dose for treating the target 101. In a fifth step 710, based on the tissue disruption rate profile (and, in some embodiments, information about the patient, such as the physiological parameter), the computational facility 126 may determine the acoustic power profile (e.g., amplitudes, frequencies, phases, directions and/or activation time associated with the transducer elements, or time intervals between consecutive series of sonications) of the ultrasound system and characteristics (e.g., a type, a dose, a concentration profile, a temperature, a maximum microbubble size, a normal microbubble size distribution around a specified mean, a mean microbubble diameter, a shell composition of the microbubbles, a gas and/or liquid core composition of the microbubbles or an administration profile) of the exogenous agent and the microbubbles carried therein. In addition, the computational facility 126 may determine a sequence of actions to activate the transducer 102 and administration system 113 based on the determined acoustic power profile and characteristics of the exogenous agent and/or therapeutic agent(s) (in a sixth step 712). Again, the created treatment plan may be stored in memory accessible to the controller 108/122/124 and/or computational facility 126 for retrieval during treatment.

Figure 7B:
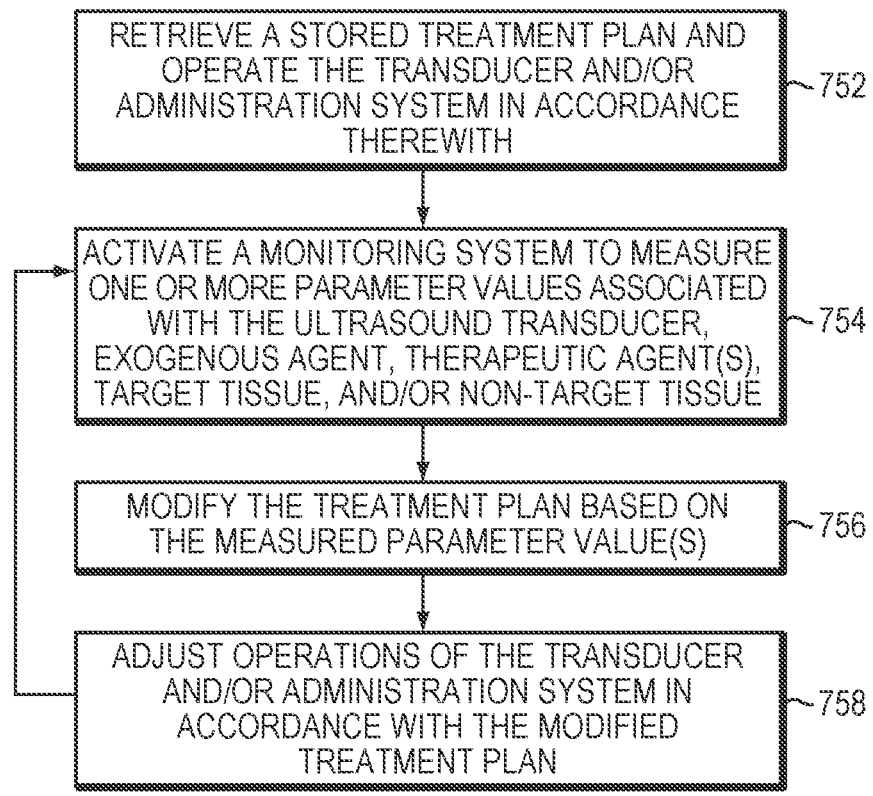
FIG. 7B is a flow chart illustrating an approach for executing and modifying a treatment plan in accordance with various embodiments of the present invention.

FIG. 7B illustrates an exemplary approach 750 for executing (and, in some embodiments, modifying) a treatment plan in accordance herewith various embodiments. As shown, during the treatment procedure, the controller 108/122/124 may access the memory to retrieve the stored treatment plan and operate the transducer 102 and the administration system 113 in accordance therewith (in a step 752). For example, the transducer elements 104 may be activated in accordance with the parameter values specified in the treatment plan to transmit high-energy ultrasound pulses focused at the target 101 for treatment (e.g., thermal ablation). In addition, the administration system 113 may sequentially or simultaneously introduce the exogenous agent and therapeutic agent(s) to the target region 101. In a second step 754, the monitoring system 112 may measure one or more parameter values associated with the ultrasound transducer, exogenous agent, therapeutic agent(s), target tissue, and/or non-target tissue during treatment. For example, the monitoring system 112 may include a biosensor for measuring a physiological parameter value (e.g., blood pressure, blood circulation rate, blood perfusion rate, blood oxygen level or heart rate) of the patient. Additionally or alternatively, the monitoring system 112 may include an imager for measuring a tissue characteristic (e.g., a temperature, a size, a shape or a location) of the target region 101 and/or non-target region. In one embodiment, the monitoring system 112 includes an acoustic-signal detector for measuring ultrasound reflections or emissions from the microbubbles at the target and/or non-target region. In a third step 756, based on the measured parameter value(s), the computational facility 126 may modify the treatment plan. Subsequently, operations of the transducer 102 and/or the administration system 113 may be adjusted in accordance with the modified treatment plan so as to achieve the desired therapeutic objective(s). Steps 754-758 may be iteratively performed throughout the entire treatment procedure.

It should be noted although the ultrasound procedure described herein is enhanced using microbubbles, the systems and methods described above may also be implemented for ultrasound procedures enhanced using other approaches. For example, emulsions and/or droplets composed of various liquid perfluorocarbon agents may be utilized to enhance the ultrasound procedure. Accordingly, the administration system 113 described herein may be used to introduce the emulsions/droplets into the target region 101, and the approaches for measuring and manipulating various characteristics of the microbubbles may be applied to measure and manipulate the characteristics (e.g., the size, shell composition (if any), liquid core composition, etc.) of the emulsions/droplets as well.

The therapeutic agent(s) may include any drug that is suitable for treating a tumor. For example, for treating glioblastoma (GBM), the drug may include or consist of, e.g., one or more of Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, Cytarabine (cytosine arabinoside, ara-C)/ara-U, etc.

In addition, for treating GBM, those skilled in the art can select a drug and a BBB opening regime optimized to enhance drug absorption across the BBB within patient safety constraints. In this regard, it is known that the BBB is actually already disrupted in the core of many tumors, allowing partial penetration of antitumor drugs; but the BBB is widely intact around the "brain adjacent to tumor" (BAT) region where invasive/escaping GBM cells can be found, and which cause tumor recurrence. Overcoming the BBB for better drug delivery within the tumor core and the BAT can be accomplished using ultrasound as described herein. The drugs employed have various degrees of toxicity and various penetration percentages through the BBB. An ideal drug has high cytotoxicity to the tumor and no BBB penetration (so that its absorption and cytotoxic effects can be confined to regions where the BBB is disrupted), low neurotoxicity (to avoid damage to the nervous system), and tolerable systemic toxicity (e.g., below a threshold) at the prescribed doses. The drug may be administered intravenously or, in some cases, by injection proximate to the tumor region.

Figure 8A:
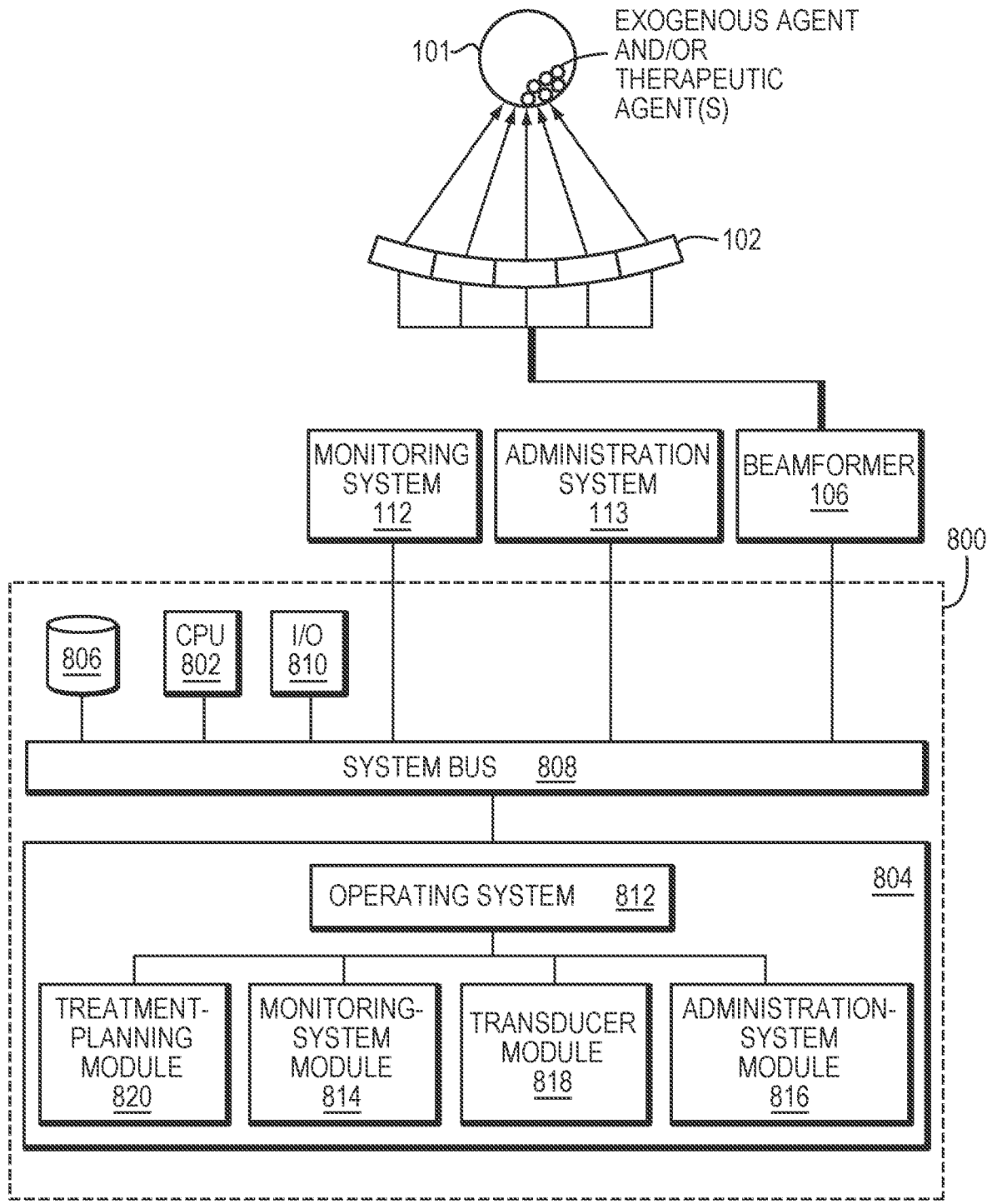
FIGS. 8A and 8B schematically illustrate exemplary systems for planning and causing execution of a microbubble-mediated ultrasound procedure in accordance with various embodiments.

Further, the computational facility 126 that facilitates treatment planning and adjustment may be implemented in the ultrasound controller 108, monitoring-system controller 122, administration-system controller 124 and/or a separate controller. The computational facility 126 may be implemented in any suitable combination of hardware, software, firmware, or hardwiring. Referring to FIG. 8A, the computational facility 126 may be provided by a suitably programmed general-purpose computer 800. The computer may include a central processing unit (CPU) 802 and system memory 804, as well as, typically, one or more non-volatile mass storage devices 806 (such as one or more hard disks and/or optical storage units). The computer 800 further includes a bidirectional system bus 808 over which the CPU 802, memory 804, and storage devices 806 communicate with each other and with internal or external input/output devices, such as traditional user interface components 810

(including, e.g., a screen, a keyboard, and a mouse) as well as the beam former 106, the monitoring system 112 and the administration system 113.

The system memory 804 contains instructions, conceptually illustrated as a group of modules, that control the operation of CPU 802 and its interaction with the other hardware components. An operating system 812 directs the execution of low-level, basic system functions such as memory allocation, file management and operation of mass storage devices 806. At a higher level, one or more service applications provide the computational functionality required for treatment planning, modification and execution. For example, as illustrated, the system may include a monitoring-system module 814 for communicating with the monitoring-system controller 124, an administration-system module 816 for communicating with the administration-system controller 124, a transducer module 818 for communicating with the transducer controller 108 of the transducer elements 104, and a treatment-planning module 820 for creating or adjusting the treatment plan that determines the sequence, locations, and treatment profile parameters of a series of sonications and administrations of the exogenous agent and/or therapeutic agent(s) based on a user input and/or the signals received from the monitoring system 112, administration system 113 and/or transducer 102; the resulting treatment plan may be used by the transducer controller 108 to determine the ultrasound parameter settings and/or by the administration system 113 to determine the characteristics of the exogenous agent and/or therapeutic agent(s).

Figure 8B:
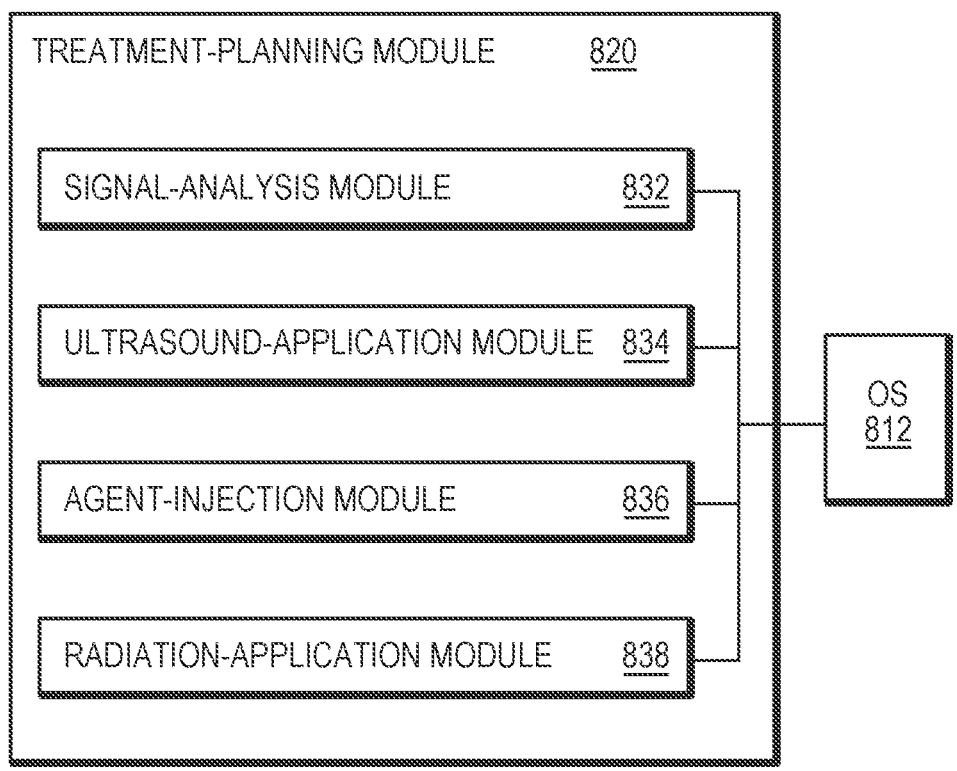

Referring to FIG. 8B, the treatment planner 820 may, itself, include a number of separate but intercommunicating modules for performing the simulation steps and functions described above. For example, the treatment planner 820 may include a signal-analysis module 832 for processing and analyzing data received from the monitoring system 112 and based thereon determine a characteristic (e.g., a temperature, a structure, a size, a shape, a location, etc.) of the target/non-target region, an ultrasound-application module 834 for computing the settings of ultrasound parameters for generating a focus having desired focusing properties at the target region, an agent-injection module 836 for determining a desired characteristic (e.g., a type, a dose, a concentration profile, a temperature, an administering rate, an administering timing, an administering pressure, etc.) of the exogenous agent and/or therapeutic agent(s) based on, for example, the received signals from the monitoring system, the desired therapeutic objective(s), the ultrasound parameter settings, the physical model and/or retrospective study of the patients experiencing microbubble-enhanced ultrasound procedure. In one embodiment, the treatment planner 820 includes a radiation-application module 838 for applying a radiation does to the target tumor tissue. The various modules utilize the techniques described above and may be programmed in any suitable programming language, including, without limitation, high-level languages such as C, C++, C#, Ada, Basic, Cobra, Fortran, Java, Lisp, Perl, Python, Ruby, or Object Pascal, or low-level assembly languages; in some embodiments, different modules are programmed in different languages. As will be readily understood by a person of skill in the art, the computational functionality required to carry out treatment-planning methods in accordance herewith may be organized (in software modules or otherwise) in many different ways, and the depicted embodiment in FIGS. 8A and 8B is, therefore, not to be regarded as limiting.

In addition, the ultrasound controller 108, the monitoring-system controller 122, the administration-system controller 124, and the computational facility 126 may be implemented in a single, integrated control facility or form two or more stand-alone devices in communication therebetween. Further, the ultrasound controller 108, the monitoring-system controller 122, the administration-system controller 124, and/or the computational facility 126 may include one or more modules implemented in hardware, software, or a combination of both as described above. Again, for embodiments in which the functions are provided as one or more software programs, the programs may be written in any of a number of high level languages such as PYTHON, FORTRAN, PASCAL, JAVA, C, C++, C #, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for microbubble-enhanced focused ultrasound treatment of target tissue, the system comprising:
an ultrasound transducer comprising a phased array of independently controllable transducer elements;
an administration device for administering an exogenous agent;
a monitoring system for measuring at least one parameter value associated with at least one of the ultrasound transducer, the exogenous agent, the target tissue, or non-target tissue;
computer memory storing a treatment plan specifying a disruption rate profile of the target tissue; and
at least one controller configured to:
(a) cause administration of the exogenous agent;
(b) drive at least some of the transducer elements at different phases to treat the target tissue by steering acoustic energy beams to the target tissue and generating a focus therein in the presence of administered exogenous agent;
(c) receive, from the monitoring system, the measured at least one parameter value indicating a treatment condition in response to administration of the exogenous agent and transmission of the ultrasound waves during treatment; and
(d) adjust a characteristic of the exogenous agent based at least in part on the measured at least one parameter value and the disruption rate profile.

2. The system of claim 1, wherein the monitoring system comprises a biosensor, and the measured at least one parameter value comprises a physiological parameter value.

3. The system of claim 2, wherein the physiological parameter value comprises at least one of a blood pressure, a blood circulation rate, a blood perfusion rate, a blood oxygen level or a heart rate.

4. The system of claim 2, wherein the treatment plan specifies the characteristic of the exogenous agent, and the at least one controller is further configured to adjust the characteristic of the exogenous agent based at least in part on the measured physiological parameter value.

5. The system of claim 4, wherein the characteristic of the exogenous agent comprises at least one of a type, a dose, a concentration profile, a temperature, or an administration profile of the exogenous agent.

6. The system of claim 5, wherein the administration profile comprises at least one of an administration rate, an administration timing or an administration pressure of the exogenous agent.

7. The system of claim 4, wherein the treatment plan specifies the disruption rate profile of the target tissue.

8. The system of claim 7, wherein the treatment plan specifies an acoustic power profile associated with the ultrasound transducer, the at least one controller being further configured to adjust the acoustic power profile based at least in part on the adjusted characteristic of the exogenous agent.

9. The system of claim 1, wherein the administration device is further configured to administer the exogenous agent, and the treatment plan specifies a characteristic of the microbubbles.

10. The system of claim 9, wherein the microbubble characteristic comprises at least one of a diameter, a size distribution, a shell composition, a gas composition and/or a liquid core composition.

11. The system of claim 1, wherein the monitoring system comprises an imager, and the measured at least one parameter value comprises a tissue characteristic of at least one of the target tissue or the non-target tissue.

12. The system of claim 11, wherein the tissue characteristic comprises at least one of a temperature, a structure, a size, a shape or a location of the target tissue.

13. The system of claim 11, wherein the treatment plan specifies a characteristic of the exogenous agent, and the at least one controller is further configured to adjust the characteristic of the exogenous agent based at least in part on the measured tissue characteristic of at least one of the target tissue or the non-target tissue.

14. The system of claim 1, wherein the monitoring system comprises an acoustic-signal detector, and the measured at least one parameter value comprises at least one of ultrasound reflections or emissions from at least one of the target tissue or the non-target tissue.

15. The system of claim 14, wherein the treatment plan specifies a characteristic of the exogenous agent, and the at least one controller is further configured to adjust the characteristic of the exogenous agent based at least in part on the measured ultrasound reflections and/or emissions.

16. The system of claim 15, wherein the treatment plan specifies an acoustic power profile associated with the ultrasound transducer, and the at least one controller is further configured to adjust the acoustic power profile based at least in part on the adjusted characteristic of the exogenous agent or the measured ultrasound reflections and/or emissions.

17. The system of claim 1, further comprising a radiation device for transmitting a radiation dose to the target tissue.

18. The system of claim 1, further comprising a second administration device for administering a therapeutic agent to the target tissue.

19. The system of claim 18, wherein the therapeutic agent comprises at least one of Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, or Cytarabine (cytosine arabinoside, ara-C)/ara-U.

20. The system of claim 18, wherein the treatment plan specifies a characteristic of the therapeutic agent, and the at least one controller is configured to adjust the characteristic of the therapeutic agent based at least in part on the measured at least one parameter value.

21. The system of claim 20, wherein the characteristic of the therapeutic agent comprises at least one of a type, a dose, a concentration profile, a temperature, an administration rate, an administration timing or an administration pressure of the therapeutic agent.

22. The system of claim 1, wherein the ultrasound transducer, monitoring system, and administration device are controlled by three separate, intercommunicating controllers.

23. The system of claim 1, wherein the ultrasound transducer and monitoring system are controlled by a first controller and the administration device is controlled by a second controller, the first and second controllers being in communication with each other, wherein the at least one controller comprises the first controller and the second controller.

24. The system of claim 1, wherein the measured at least one parameter value is indicative of the treatment condition in response to an interaction between the administered exogenous agent and the transmitted ultrasound waves.

25. A system for microbubble-enhanced focused ultrasound treatment of target tissue, the system comprising:
an ultrasound transducer comprising a phased array of independently controllable transducer elements;
an administration device for administering at least one of an exogenous agent or a therapeutic agent;
a monitoring system for measuring at least one parameter value associated with at least one of the ultrasound transducer, the exogenous agent, the therapeutic agent, the target tissue, or non-target tissue;
computer memory storing a treatment plan that specifies a disruption rate profile of the target tissue, and a series of operations of the ultrasound transducer and the administration device so as to achieve a desired treatment effect on the target tissue; and
a controller configured to:
drive (i) at least some of the transducer elements of the ultrasound transducer at different phases to treat the target tissue by steering acoustic energy beams to the target tissue and generating a focus therein in the presence of administered exogenous agent or administered therapeutic agent and (ii) the administration device, based at least in part on the treatment plan; and
adjust a characteristic of the exogenous agent or the therapeutic agent based at least in part on the measured at least one parameter value and the disruption rate profile.

* * * * *